US012614037B2

(12) United States Patent
De Luis Balaguer et al.

(10) Patent No.: US 12,614,037 B2
(45) Date of Patent: Apr. 28, 2026

(54) LARGE LANGUAGE MODEL INTERFACE FOR COMPLEX DATABASES

(71) Applicant: MICROSOFT TECHNOLOGY LICENSING, LLC, Redmond, WA (US)

(72) Inventors: Maria Angels De Luis Balaguer, Redmond, WA (US); Sara Malvar Maua, Sao Paulo (BR); Swati Sharma, Hayward, CA (US); Ranveer Chandra, Kirkland, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 137 days.

(21) Appl. No.: 18/429,150

(22) Filed: Jan. 31, 2024

(65) Prior Publication Data

US 2025/0245215 A1 Jul. 31, 2025

(51) Int. Cl.
G06F 40/30 (2020.01)
G06F 16/242 (2019.01)
G16B 50/00 (2019.01)

(52) U.S. Cl.
CPC .......... G06F 40/30 (2020.01); G06F 16/2425 (2019.01); G06F 16/243 (2019.01); G16B 50/00 (2019.02)

(58) Field of Classification Search
None
See application file for complete search history.

(56) References Cited

U.S. PATENT DOCUMENTS

| | | | | |
|---|---|---|---|---|
| 8,719,005 | B1* | 5/2014 | Lee | G06N 5/025 |
| | | | | 707/706 |
| 11,966,704 | B1* | 4/2024 | Magary | G06F 40/30 |
| 12,306,828 | B1* | 5/2025 | Chakraborty | G06F 16/24522 |
| 12,353,407 | B1* | 7/2025 | Shachaf | G06F 16/243 |
| 2011/0314006 | A1* | 12/2011 | Sweeney | G06F 16/951 |
| | | | | 707/723 |
| 2024/0320445 | A1* | 9/2024 | Mallick | G06F 40/30 |
| 2024/0362212 | A1* | 10/2024 | Sun | G06F 16/24522 |

(Continued)

OTHER PUBLICATIONS

Jamil, Hasan M. "Knowledge rich natural language queries over structured biological databases." Proceedings of the 8th ACM international conference on bioinformatics, computational biology, and health informatics. 2017. (Year: 2017).*

*Primary Examiner* — Douglas Godbold
(74) *Attorney, Agent, or Firm* — Newport IP, LLC; Benjamin A. Keim

(57) ABSTRACT

This disclosure introduces a novel method and system for using a large language model (LLM) to create a convenient interface for a complex database. The system includes a custom prompt generator that creates custom prompts from natural language queries. The custom prompts are used to control how the LLM interacts with a database look-up tool. The database look-up tool provides queries to the database in a format understandable by the database and receives responses from the database. This system is useful for obtaining information that is not in a natural language, and thus, is poorly suited for being processed as an embedding by the LLM. Information obtained from the database is included in an answer produced by the LLM.

20 Claims, 5 Drawing Sheets

(56) References Cited

U.S. PATENT DOCUMENTS

| | | | |
|---|---|---|---|
| 2024/0394285 A1* | 11/2024 | Cunningham | H04L 51/02 |
| 2024/0403373 A1* | 12/2024 | Chao | G06F 16/9538 |
| 2025/0045530 A1* | 2/2025 | Reddy | G06F 40/40 |
| 2025/0086213 A1* | 3/2025 | Dilipkumar | G06F 16/24522 |
| 2025/0103592 A1* | 3/2025 | Niu | G06F 40/295 |
| 2025/0124024 A1* | 4/2025 | Kirk | G06F 21/602 |
| 2025/0156413 A1* | 5/2025 | Barkan | G06F 40/295 |
| 2025/0156574 A1* | 5/2025 | Eberlein | G06F 16/33295 |
| 2025/0173330 A1* | 5/2025 | Durg | G06F 16/243 |
| 2025/0210033 A1* | 6/2025 | Sharifi | G06F 16/33295 |
| 2025/0217351 A1* | 7/2025 | Tan | G06F 16/2423 |

* cited by examiner

CHAT INTERFACE 100

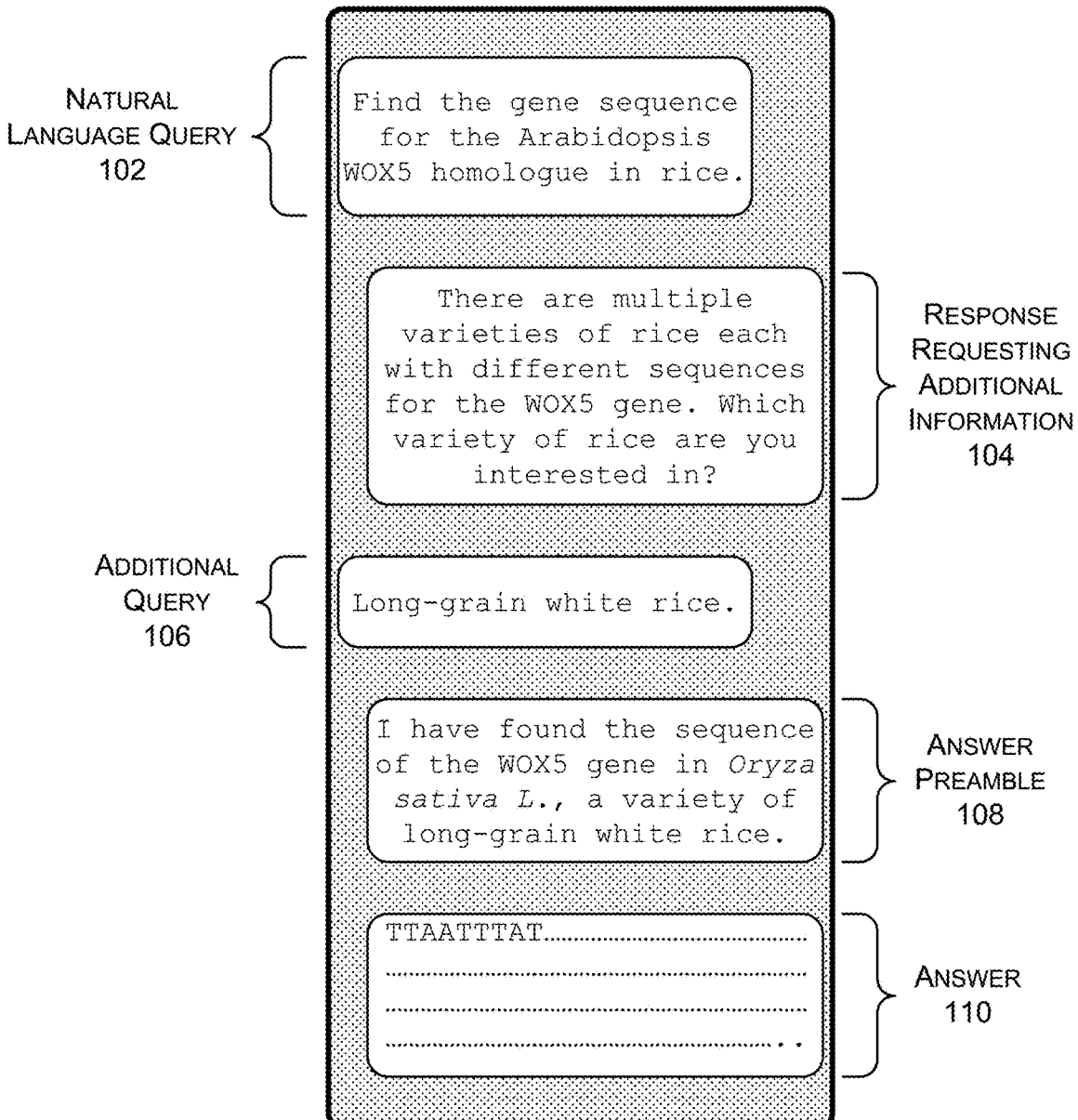

NATURAL LANGUAGE QUERY 102

Find the gene sequence for the Arabidopsis WOX5 homologue in rice.

There are multiple varieties of rice each with different sequences for the WOX5 gene. Which variety of rice are you interested in?

RESPONSE REQUESTING ADDITIONAL INFORMATION 104

ADDITIONAL QUERY 106

Long-grain white rice.

I have found the sequence of the WOX5 gene in *Oryza sativa L.*, a variety of long-grain white rice.

ANSWER PREAMBLE 108

TTAATTTAT..................................
..................................
..................................
.......................... . .

ANSWER 110

FIG. 1

REFERENCE TO A BIOLOGICAL SEQUENCE 202
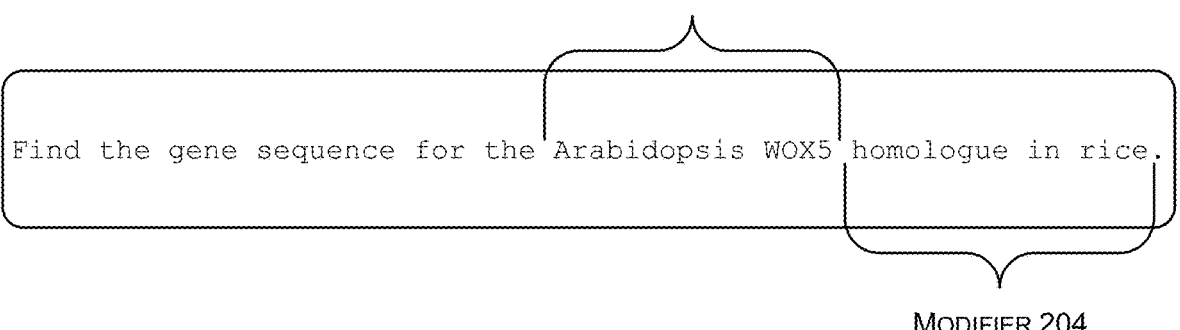
Find the gene sequence for the Arabidopsis WOX5 homologue in rice.
MODIFIER 204
NATURAL LANGUAGE QUERY 102
VARIABLE 206
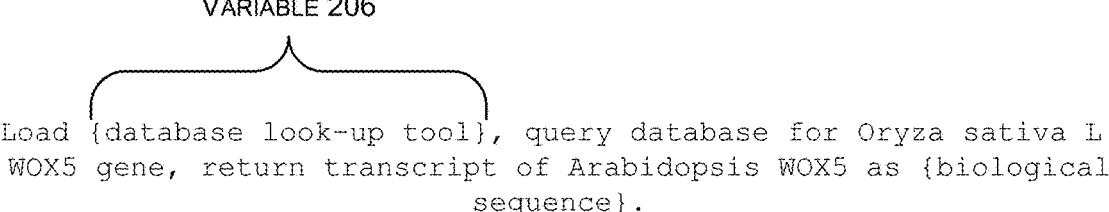
Load {database look-up tool}, query database for Oryza sativa L. WOX5 gene, return transcript of Arabidopsis WOX5 as {biological sequence}.
CUSTOM PROMPT 200
FIG. 2

400

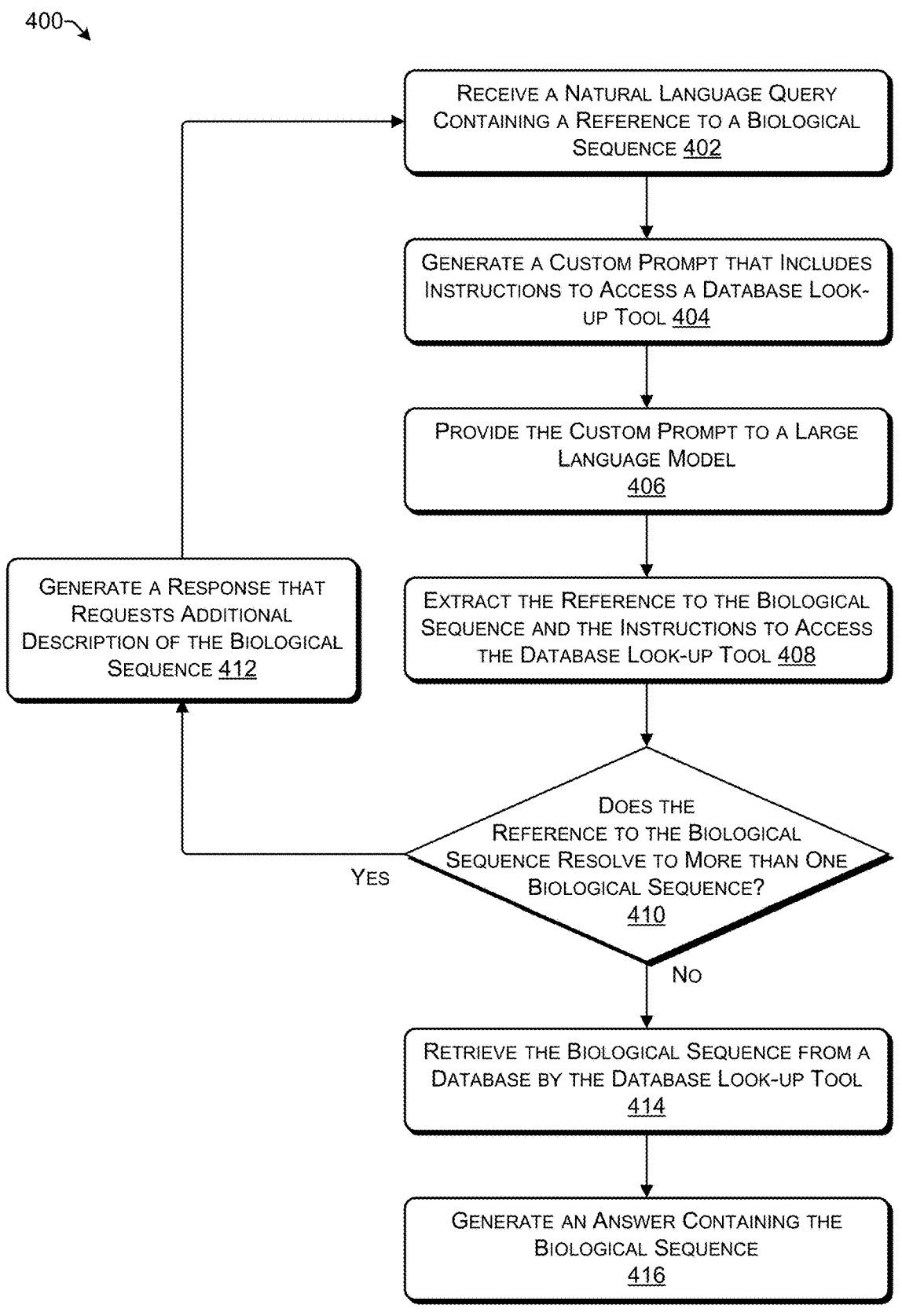

RECEIVE A NATURAL LANGUAGE QUERY CONTAINING A REFERENCE TO A BIOLOGICAL SEQUENCE 402

GENERATE A CUSTOM PROMPT THAT INCLUDES INSTRUCTIONS TO ACCESS A DATABASE LOOK-UP TOOL 404

PROVIDE THE CUSTOM PROMPT TO A LARGE LANGUAGE MODEL 406

GENERATE A RESPONSE THAT REQUESTS ADDITIONAL DESCRIPTION OF THE BIOLOGICAL SEQUENCE 412

EXTRACT THE REFERENCE TO THE BIOLOGICAL SEQUENCE AND THE INSTRUCTIONS TO ACCESS THE DATABASE LOOK-UP TOOL 408

DOES THE REFERENCE TO THE BIOLOGICAL SEQUENCE RESOLVE TO MORE THAN ONE BIOLOGICAL SEQUENCE? 410

YES

NO

RETRIEVE THE BIOLOGICAL SEQUENCE FROM A DATABASE BY THE DATABASE LOOK-UP TOOL 414

GENERATE AN ANSWER CONTAINING THE BIOLOGICAL SEQUENCE 416

FIG. 4

LARGE LANGUAGE MODEL INTERFACE FOR COMPLEX DATABASES

BACKGROUND

There is a large amount of information available in complex databases that is difficult to access because of the complexity of using the databases. Some of this is due to characteristics of the information in the databases. For example, some types of information are difficult to index using keywords, the information may be incomplete or inconsistent, or a human user may not be able to readily inspect a response and appreciate if it is correct or not. Some of the difficulties may be due to database design. Databases that provide sophisticated ways to search and access complex information may have a complex interface for which there is a learning curve to use effectively.

Databases do not serve their purpose when information inside them is inaccessible to the people who need it. Improvements in database interfaces can make it easier for users to access information in complex databases. This disclosure is made with respect to these and other considerations.

SUMMARY

This disclosure pertains to the use of a large language model (LLM) to facilitate information retrieval from a database. The LLM is trained to understand natural language inputs and can interact with a user through a chat interface. This allows the user to interact with the database using natural language queries and refine or modify queries through a "conversational" interaction with the LLM. Users without any prior knowledge of the commands and features are able to easily query the database and receive answers.

The natural language query provided by the user is first processed by a custom prompt generator. The custom prompt generator converts the natural language input into a prompt that is provided to the LLM. The custom prompt generator may rearrange the natural language query and may add additional prompting text to shape the response of the LLM. The custom prompt generator also includes in the prompt instructions to access a database look-up tool.

The database look-up tool is a software tool, separate from the LLM, that is designed to interface with a database. That database look-up tool may be programmed with specific commands, such as API calls, for interacting with a specific database. Instructions to use the database look-up tool may be explicitly added as additional words in the custom prompt or the custom prompt may contain a variable that references the database look-up tool. Thus, only the variable (e.g., use {database look-up tool}) would be included in the custom prompt rather than an explicit description of the tool's functionality.

The custom prompt is parsed by the LLM to understand what information the user is seeking and which tools to use. Interaction between the database look-up tool, the LLM, and the database may be managed by an orchestration framework that enables the different components to work together and share information. Thus, the database look-up tool operates under the control of the LLM and queries the database according to the LLM's understanding of the custom prompt.

The database look-up tool may comprise multiple separate tools. Those separate tools may be chained together such that the output from one tool becomes the input to the next tool. For some databases, responses to queries may contain irrelevant information or the relevant information may be combined with other data. For example, the database may return a whole webpage of text in response to a query, but the desired information is only a single identifier number located somewhere on that webpage. Thus, the database look-up tool may also include regular expression searching to extract specific information from the results.

Once the information sought by the natural language query is retrieved from the database, the LLM provides that information to the user. This may be in the same format or interface that the user used to provide the natural language query (e.g., a chat interface). If there are ambiguities in the natural language query or the LLM needs more information to query the database, the LLM can respond in natural language with a request for additional information.

Features and technical benefits other than those explicitly described above will be apparent from a reading of the following Detailed Description and a review of the associated drawings. This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter. The term "techniques," for instance, may refer to system(s), method(s), computer-readable instructions, module(s), algorithms, hardware logic, and/or operation(s) as permitted by the context described above and throughout the document.

BRIEF DESCRIPTION OF THE DRAWINGS

The Detailed Description is described with reference to the accompanying figures. In the figures, the left-most digit(s) of a reference number identifies the figure in which the reference number first appears. The same reference numbers in different figures indicate similar or identical items. References made to individual items of a plurality of items can use a reference number with a letter of a sequence of letters to refer to each individual item. Generic references to the items may use the specific reference number without the sequence of letters.

FIG. 1 is a diagram of a chat interface showing a conversation between a user and a LLM that provides a biological sequence as an answer.

FIG. 2 is an illustration of a natural language query and a custom prompt.

FIG. 4 is a flowchart of a method for using a LLM to obtain a biological sequence from a database.

DETAILED DESCRIPTION

Figure 3:
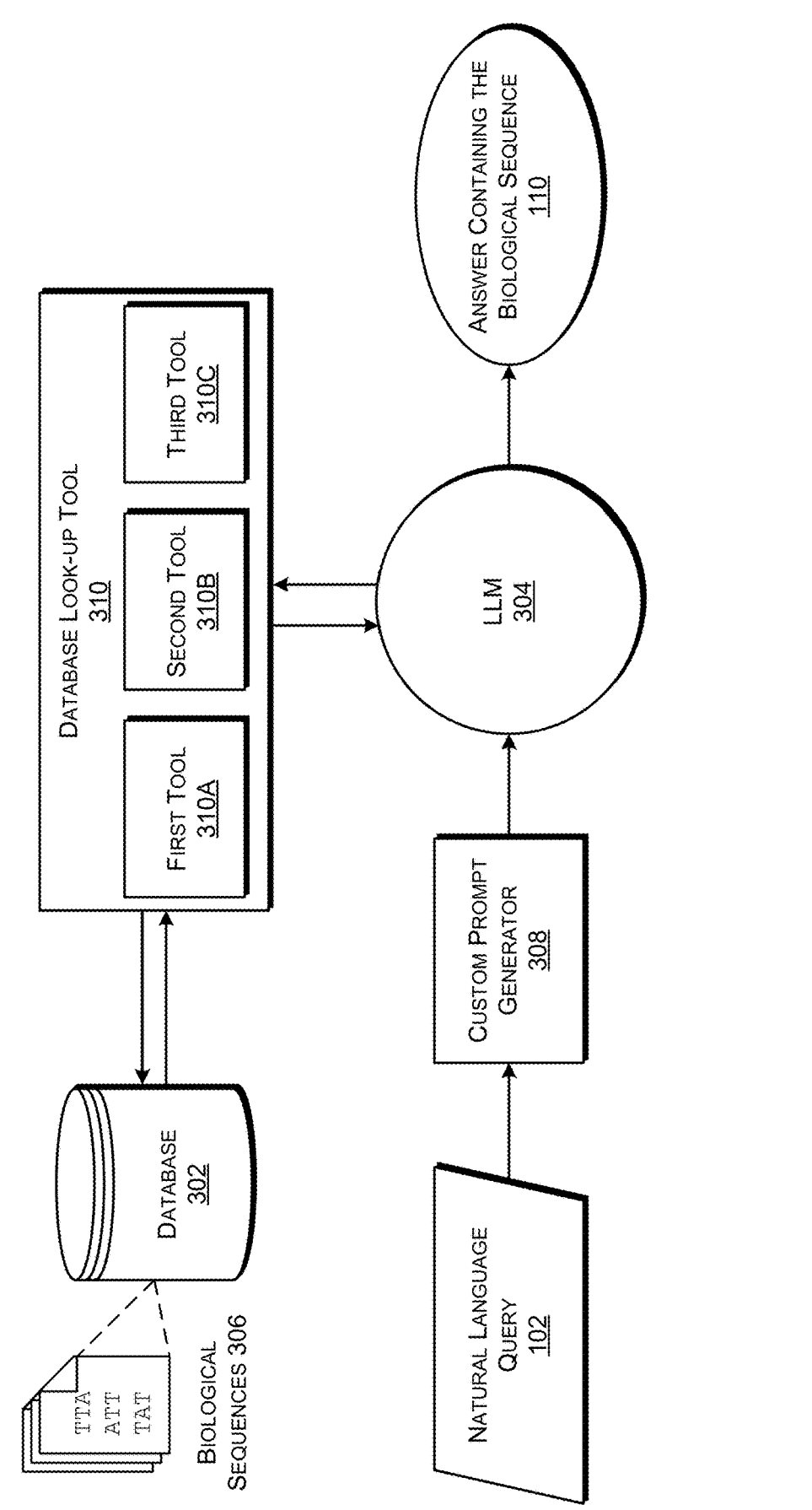
FIG. 3 is a diagram of a framework for accessing a database using an LLM.

This disclosure provides an LLM interface for accessing complex databases. In particular, this disclosure is related to using an LLM for obtaining biological sequences such as gene sequences and protein sequences without the need to understand the specifics of interacting with a database containing such sequences.

LLMs, such as GPT4, GPT3, and BERT, are proficient at addressing complex problems in genomics and bioinformatics. They can respond to detailed queries and even generate code to find solutions to certain problems. However, LLMs trained on natural language cannot directly apply these solutions to actual biological sequences. Even though biological sequences can be represented by strings of letters like natural language, LLMs are not equipped to interpret embeddings created from biological sequences. Providing a biological sequence to an LLM, or asking an LLM to generate a biological sequence, in a way that requires the LLM to build an embedding from the biological sequence will generally fail.

The challenge of processing biological sequence data for an LLM arises from several factors. Biological sequences, whether they are genomic (composed of the nucleotide representations A, T, C, and G) or protein sequences (composed of one or three letter representation of amino acids), lack the contextual and semantic information that LLMs are designed to understand. Biological sequences can be extraordinarily lengthy, often extending to millions or even billions of characters. The computational intensity of processing such long sequences may exceed a LLM's input length limit. Biological sequences frequently contain repetitive patterns, which can pose a challenge for an LLM to interpret in a meaningful way. The interpretation of biological data often requires specialized biological knowledge, such as understanding the relationships between sequences, genes, proteins, and phenotypes. While an LLM can be trained on a wide array of topics, one trained on natural language text will lack the knowledge required for accurate interpretation of biological sequences.

To deal with the inability of LLMs to effectively process biological sequences, the methods and systems of this disclosure leverage the capabilities of LLMs to access complex databases that contain biological sequences. The abilities of LLMs are used to interpret queries and determine what information to request from a database. Thus, with this connection to a database, an LLM is able to answer concrete questions involving biological sequences. These systems and techniques have applications on comparative analyses across major lineages, identification of genomic features and patterns, and protein studies.

FIG. 1 is a diagram of a chat interface 100 showing a conversation between a user and an LLM. The LLM may be any type of LLM such as a generative pretrained transformer. Other types of LLMs besides those currently in use and other architectures including those not yet developed are also contemplated as suitable LLMs. The LLM is trained on a corpus of natural language material including material relevant to the subject matter of the database that is being accessed. For example, when the database contains biological sequences, the LLM will be trained on material that includes text relevant to biological sequences such as peer-review articles and textbooks about biology and chemistry. Most LLMs, being large language models, are trained on a variety of material and will be able to properly interpret prompts related to various technical subjects. However, if there was a language model that was not trained on the subject matter contained in the databases (e.g., trained only on fiction writing without training on scientific material) it might struggle to properly interpret the natural language prompts.

In this example, a user provides a natural language query 102. However, it is also possible that the natural language query 102 is generated programmatically by other software tools (including another LLM) or piped in from a different tool. The natural language query 102 is not limited to those created directly by a human user. The user (or other software tool) does not need to know the specifics of how to use a database or even which database to query. In this example, the natural language query 102 is asking for a specific gene sequence. This is a retrieval task. However, the natural language query 102 may be used for other types of tasks and queries that are more complex the simply retrieving a biological sequence. It may be used to make comparisons, find genes or proteins with specific characteristics, identify homologues, evaluate the accuracy of statements, or any other type of query that can be evaluated by an LLM.

The natural language query 102 is interpreted by the LLM. The LLM may determine that additional information is needed to answer the natural language query 102. If so, the LLM can generate a response requesting additional information 104. This response 104 explains what additional information is needed and may include a question to the user.

The user then responds to the response requesting additional information 104 with an additional query 106 that modifies, clarifies, or limits the initial natural language query 102. These types of iterative interactions in the chat interface 100 allow the LLM to guide the user through interactions with the database without the user needing to directly interact with the database. Additionally, the LLM may use general knowledge from its training that is not specific to the database to help the user improve the query 102 and use the database more successfully. Only one round of back-and-forth is illustrated in the chat interface 100, but it is understood that the LLM can repeatedly ask the user for additional information to refine and clarify the intended query.

The LLM processes the text of natural language query 102 and any additional queries 106 to determine what information to retrieve from the database. In the context of search for biological sequences, that information will typically include a biological sequence. The LLM may initially provide an answer preamble 108 that identifies the information retrieved from the database. The answer preamble 108 may include a common name or an identifier for the biological sequence. The answer preamble 108 may also include an explanation of how the LLM interpreted the natural language query 102 and the additional query 106 to determine what to search for in the database.

The answer 110 includes the information retrieved from the database. That information may be a biological sequence when accessing a database that includes biological sequences. This portion of the answer 110 is not generated by the LLM in the way it generates natural language answers but is pulled in from the database. In some implementations, a biological sequence from the database may be modified to remove additional characters and descriptions so that the answer 110 includes only the biological sequence. For example, many files from databases of biological sequences (even simple text files) may include words such as the name of the sequence, special characters such as those indicating the start of a sequence, accuracy scores, etc. All of these may be removed so that the answer 110 includes only the sequences. This may facilitate the user cutting and pasting the text from the answer 110 to use elsewhere. It may also facilitate automated pipelines in which the biological sequence obtained by the LLM is provided to downstream software for further analysis or processing.

However, in some implementations the answer preamble 108 and the answer 110 may be combined. For example, a single chat bubble may include both the name of the biological sequence identified and the sequence itself. The answer preamble 108 may also be omitted entirely so that the user receives as the answer 110 only the biological sequence.

FIG. 2 is an illustration of additional details of a natural language query 102 and a custom prompt 200. The natural language query 102 introduced in FIG. 1 may be any type of natural language input. Because it is in natural language, the query 102 may be freely structured without a need to understand or comply with rules for querying a specific database. In the context of searching for biological sequences, the natural language query 102 will typically include a reference to a biological sequence 202. That reference may be, but is not limited to, a common name, a known identifier or reference number such as an accession number. It may also include all or part of the biological sequence itself.

The natural language query 102 may be simple or complex. The natural language query 102 may simply state: "What is the sequence of BRCA1?" For such a query 102, the answer will be the sequence indicated in the reference to the biological sequence 202. The natural language query 102 may be complex and ask for a sequence that is different than the sequence identified in the reference to the biological sequence 202. The LLM may understand this by interpreting one or more modifiers 204 in the natural language query 102. A modifier 204 changes the biological sequence that is retrieved from the database. In FIG. 2, the reference to the biological sequence 202 specifies an *Arabidopsis* gene and the modifier 204 changes that to ask for a homologous gene in a different plant—rice. The natural language query 102 could also request a biological sequence for a gene or protein from a species or variety that includes specific characteristics such as drought tolerance. The modifier 204 may be any type of modifier that can be found in natural language. The natural language query 102 may include multiple modifiers. For example, a natural language query 102 could ask for a protein sequence of a protein that is toxic to weevils and soluble in oil. Modifiers 204 may also be included in the additional query 106.

FIG. 2 also provides an example of a custom prompt 200. The system of this disclosure does not pass the text of the natural language query 102 directly to the LLM. The query 102 provided by the user (or another computer system) is processed to generate a custom prompt 200 that is provided to the LLM. The custom prompt 200 guides the LLM to use database look-up tools provided to answer the natural language query 102. Prompt engineering, or intentional design of a string of natural language input to elicit a specific type of response from a LLM, can significantly affect the output of an LLM. The custom prompt 200 is generated from the natural language query 102 and any additional queries 106 to create an input that will cause the LLM to access a database and retrieve the desired information. For example, the custom prompt 200 may rephrase the natural language query 102, the additional query 106, and responses from the LLM into a single prompt.

The custom prompt 200 may include variables 206 which are represented in FIG. 2 by curly braces. One type of variable 206 represents a database look-up tool. The database look-up tool is a software tool different from the LLM that facilitates interaction with the database. For example, the database look-up tool may be programmed with specific rules and APIs for accessing a database. Thus, the custom prompt 200 may communicate the database look-up tool to be used by the LLM through inclusion of a variable 206 in the custom prompt 200. Alternatively, a description of the database look-up tool and commands to use it may be provided directly in the custom prompt 200 without the use of a variable 206.

Variables 206 may also be used to represent other information in the custom prompt 200. For example, the information to be retrieved from the database that is not generated by the LLM—a biological sequence in the current example—can be represented as a variable 206. This informs the LLM that it does not need to generate the biological sequence but can simply plug in the information retrieved from the databases that corresponds to the variable 206.

FIG. 3 is a diagram of a framework 300 for accessing a database 302 using an LLM 304. The framework 300 is a representation of logical components, information, software components, and interactions between them that enable operation of the systems and methods of this disclosure. The database 302 may be any type of database such as a complex database that stores biological sequences 306. Examples of publicly available databases that contain biological sequences 306 include NCBI, ENA, and EMBL. NCBI (the National Center for Biotechnology Information) database includes GenBank. ENA (European Nucleotide Archive) is a repository for annotated DNA and RNA sequences. The EMBL (European Molecular Biology Laboratory) database includes nucleotide sequence data and related biological information. The framework 300 begins with a natural language query 102 as introduced in FIG. 1. Although this example references a biological sequence 306, the natural language query 102 may be generalized to include other types of information that is not amenable to processing through embeddings generated by LLMs.

The natural language query 102 is received and processed by a custom prompt generator 308. The custom prompt generator 308 is configured to generate a custom prompt 200 such as that shown in FIG. 2 from the natural language query 102. The custom prompt includes instructions to process the query 102, access an appropriate database look-up tool 310, and parse the final output which is an answer 110 containing the biological sequence. The custom prompt generator 308 provides the custom prompt to the LLM.

The prompt may be implemented in whole or part by the custom prompt generator 308 through an orchestration framework designed for the development of applications using LLMs. For example, the orchestration framework can fill in variables in the prompt with the specific implementation details or instructions. The orchestration framework provides tools and APIs that simplify the process of building systems that include LLMs. The orchestration framework also makes it possible for an LLM to integrate with external data sources such as the database 302. Persons of ordinary skill in the art will understand how to use an orchestration framework to integrate an LLM with other tools and data sources. One example of such an orchestration framework is LangChain which is available on the World Wide Web at langchain.com. There are other orchestration frameworks such as TensorFlow and Semantic Kernel by Microsoft®.

The custom prompt generator 308 writes the prompts that are provided to the LLM 304. As mentioned in the discussion of FIG. 2, the prompts may include reference to the database look-up tool 310 as a variable. This creates a placeholder in the prompt that will be filled with the output or functionality of the specific tool. This allows the LLM 304 to incorporate information or actions from external sources directly into its responses, enhancing its capabilities and flexibility. The custom prompt generator 308 may use prompt templates that define the structure of the prompts sent to the LLM 304. These templates can contain variables, represented by placeholders like {tool} or {tool_output}. As the prompt is generated, the custom prompt generator 308 replaces the tool variables with the appropriate tool names or the actual output from those tools. The LLM 304 then receives the prompt with the tool information integrated into it. The LLM 304 processes the prompt, incorporating the tool-provided data or functionality into its response.

The LLM 304 interacts with the database look-up tool 310 referenced in the custom prompt generated by the custom prompt generator 308. The custom prompt guides the LLM 304 in interpreting the query 102 and extracting the reference to the biological sequence 306 from the natural language query 102. The custom prompt also instructs the LLM 304 to use the database look-up tool 310 to extract the biological sequence 306 from the database 302. Finally, the custom prompt can guide the LLM 304 in parsing the output received from the database 302 and returning the biological sequence 306 as an answer.

The database look-up tool 310 may represent a single tool or a toolbox of multiple tools that communicate with the database 302. The database look-up tool 310 is configured to submit queries and obtain data from the database 302. The communication may be through APIs exposed by the database 302. The database look-up tool 310 may include additional ways of interacting with the content of the database 302 such as regular expression searching. The specific functionality of the database look-up tool 310 may vary depending on the database 302. For example, different databases 302 may be accessed by different APIs. Each database 302 may have a different database look-up tool 310 programmed with its specific APIs. In some implementations, the database look-up tool 310 represents multiple different tools each configured to work with a different database 302.

In some implementations, the database look-up tool 310 includes multiple different tools chained together so that the output of one tool is the input for a second tool. A first tool 310A searches the database 302 with the reference to the biological sequence 306 provided in the natural language query 102. This is typically the common name of a gene. In some implementations, the LLM 304 may generate synonyms to the common name and the first tool 310A may submit multiple queries to the database 302—one for each synonym. The same gene may have different names due to the presence of multiple reference genomes for an organism, change in naming convention, evolution of scientific understanding such as realizing that a sequence represents multiple different genes, or for other reasons. The database 302 returns a database-specific gene identifier (ID) for the gene indicated by common name. A gene ID is used to identify a specific gene. A gene may include multiple sections of coding sequences. So, the same nucleotide sequence may be labeled as a coding sequence (CDS) and a gene. This first tool 310A functions as a gene ID lookup tool.

A second tool 310B uses the database-specific identifier retrieved by the first tool 310A to search the database 302 for a sequence identifier that provides a more specific identifier for a particular biological sequence rather than simply identify a gene. This sequence identifier may be a transcript ID for a gene or a protein ID for a protein. Sequence identifiers are used to track and reference specific sequences in the database 302. A sequence identifier may include a GenInfo Identifier (GI) number and version number. In some databases, each time a sequence record is changed, it is assigned a new GI number. A sequence version may be used to group all of the GI numbers for a specific sequence into an ordered series.

Querying the database 302 with the gene ID may return a lot of information about the gene beyond just the DNA sequence of the gene or peptide sequence of a protein coded for by the gene. This information, which may be a file, the content of a webpage, or some other format, can then be searched to find the sequence identifier from the query. For some database, the information will be structured in such a way that the sequence identifier can be located based on knowledge of how the information is structured. For example, the database may return text (e.g., webpage or other text) that has an indicator or identifier of the sequence identifier. The sequence identifier may be presented between or beside certain characters such as "*<ID>*" or "Sequence ID: <ID>" The database may also return structured text such as XML in which the sequence identifier is flagged as such. The specific characters, key words, or markup language tags will vary with the output of a particular database 302. The second tool 310B is programmed with the appropriate terms for searching the information returned from the database 302. Regular expression searching, or another search technique, may be used to find the sequence identifier among the information returned from the database 302. This second tool 310B functions as a sequence ID retrieval tool.

A third tool 310C uses the sequence identifier obtained by the second tool 310B to return the biological sequence 306. This is the actual nucleotide or protein sequence that was referenced in the natural language query 102. Depending on the structure of the database 302 and the type of information sought, it may be necessary to sequentially request and obtain progressively more precise indicators of the desired biological sequence 306. This third tool 310C functions as a sequence retrieval tool. The LLM 304 may remove parts of the response from the third tool 310C that are not the letters representing the biological sequence 306. In this way the LLM 304 is able to obtain a biological sequence 306 from the database 302 starting only with a common name (or other reference to the biological sequence).

FIG. 4 is a flow diagram of an illustrative method 400 for using a LLM to obtain a biological sequence from a database. Method 400 may be performed using the framework illustrated in FIG. 3.

At operation 402, a natural language query containing a reference to a biological sequence is received. The natural language query may be provided by a user through a "chat" interface or other type of interface. The natural language query could alternatively be generated by software such as another LLM.

The biological sequence may be a polynucleotide or polypeptide sequence such as a gene sequence or a protein sequence. The reference to the biological sequence may be a common name of a gene or protein. However, the reference to the biological sequence may take other forms such as an identifier or ascension number. It is also possible that the reference to the biological sequence does not specifically identify a sequence by name or number but describes characteristics of the sequence. For example, the reference to the biological sequence could be a description such as "a gene from a flowering plant associated with root growth that promotes drought hardiness."

In some implementations, the natural language query also contains a modifier that modifies the reference to the biological sequence. For example, if the reference to the biological sequence is "WOX5 in *Arabidopsis*", and the modifier is "homologue in rice" then the modification will be to search for the WOX5 gene in rice rather than *Arabidopsis*.

At operation 404, a custom prompt that includes instructions to access a database look-up tool is generated. The custom prompt is generated by a custom prompt generator that creates a prompt from the natural language query received at operation 402. The custom prompt is designed to shape the behavior of the LLM so that it uses a database to retrieve an answer to the query. In some implementations, the custom prompt represents the database look-up tool by a variable. The variable instructs the LLM to call the functionality of the database look-up tool without explicitly describing the functioning of the database look-up tool. The custom prompt may also include reference to the output from the database as a variable. In alternative implementations, the database look-up tool is not represented by a variable but included as language in the custom prompt telling the LLM how to perform the functionality of the tool.

At operation 406, the custom prompt is provided to an LLM. Interaction between the custom prompt generator and the LLM may be facilitated by an orchestration framework for the LLM. Surprisingly, it has been identified that the LLM Chat GPT4 provides more accurate answers to the natural language query when the database look-up tool is represented as a variable. Without being bound by theory, it is believed that the additional language in the custom prompt describing the tool when it is not represented as a variable makes it more difficult for the LLM to properly interpret the prompt. Thus, shorter prompts in which the database look-up tool is succinctly represented as a variable obtain better results from the LLM.

At operation 408, the reference to the biological sequence and the instructions to access the database look-up tool are extracted. The LLM identifies in the custom prompt the tool to be used and the biological sequence that is sought from the database. Thus, the LLM knows what database look-up tool to use and what biological sequence to search for.

At operation 410, it is determined if the reference to the biological sequence resolves to more than one biological sequence. Based on its knowledge from training on a corpus of relevant material, the LLM may know that the reference to the biological sequence in the natural language query received at 402 does not include enough information to identify a single biological sequence. This ambiguity may also be determined by querying the database and evaluating the response to determine that more that one biological sequence is be returned.

If there is more than one biological sequence that could be an answer to the query, the method 400 proceeds along the "yes" path to operation 412. If it does not, meaning that the reference to the biological sequence resolves to one unique sequence, the method 400 proceeds along the "no" path to operation 414.

At operation 412, the LLM generates a response that requests an additional description of the biological sequence. One example of this type of response is the response requesting additional information 104 shown in FIG. 1. This response may be generated by the LLM using knowledge from its training on a corpus of material that includes material relevant to the natural language query (e.g., in this example related to genes and/or proteins). The response requesting additional information is intended to clarify the query so that the LLM can search the database for one specific sequence. There may be multiple iterations of questions and answers between the LLM and the user (or other system that provides the query). This can continue until the LLM has collected enough information to unambiguously identify a single biological sequence.

However, in some implementations ambiguity may be tolerated and the method 400 does not generate the responses at operation 412. In such implementations, the LLM interprets the natural language prompt to identify a suitable answer even if it is not the only answer. For example, the natural language prompt may identify a gene that has slightly different sequences in multiple reference genomes. Rather than asking the user which reference genome to pull the gene sequence from (because the user may not know or care) the LLM can select one. There are many possible ways the LLM could make such a selection. One way is based on the frequency of use in its training corpus. The reference genome that is most commonly used may be selected. Another way is to select the most recent biological sequence. Some biological sequences may be updated periodically as new experiments are conducted and new sequences obtained. Rather than asking which version of a biological sequence to retrieve, the LLM may select the most recent sequence without user input.

At operation 414, the biological sequence is retrieved from the database by the database look-up tool. The database look-up took operates under control of the LLM. Interaction between the database look-up tool and the LLM may be facilitated by an orchestration framework. The database look-up tool is configured to query a database and process responses received from the database. Thus, retrieving the biological sequence may be implemented by the database look-up took querying the database with the reference to the biological sequence received at operation 402 and receiving the biological sequence.

The database look-up tool may comprise multiple tools. In some implementations, the multiple tools are chained together so that the output from one tool becomes the input to the next tool. For example, the database look-up tool may include three tools chained together. In an implementation the three tools are a first tool that is a gene ID look-up tool, a second tool that is a sequence ID retrieval tool, and a third tool that is a sequence retrieval tool.

The first tool queries the database with the reference to the biological sequence and retrieves a database-specific gene identifier. For example, the first tool may query the database with the common name of a gene provided in the natural language query and retrieve a code or number that, for the specific database, identifies that gene. The second tool uses this database-specific gene identifier to query the database and retrieve a sequence identifier for a specific sequence. A gene may be associated with multiple sequences. For example, there may be a sequence for the full length of the gene as well as just for the coding region. Additionally, there may be the DNA sequence for a gene and the protein sequence for a protein encoded by that gene. For example, the sequence identifier identifies a specific gene transcript ID or a protein ID. In some implementations, the second tool uses regular expression searching to find the sequence identifier in the results retrieved from the database. The third tool queries the database with the sequence identifier and retrieves the corresponding biological sequence.

At operation 416, an answer containing the biological sequence is generated. The answer may simply be the biological sequence with no additional description or information. The answer may be provided in the same user interface (e.g., chat interface) that received the natural language query. The answer may also be provided to another software program or tool. In some implementations the LLM also generates text to accompany the biological sequence. One example of this is the answer preamble 108 shown in FIG. 1. This additional text may identify the biological sequence and explain any decisions made by the LLM in selecting the biological sequence to retrieve. For example, if there was ambiguity in the which biological sequence to search for the answer may include an explanation of how the specific sequence was selected. For example, the answer may explain that the biological sequence came from the most-recently uploaded variant of the species in the database.

Figure 5:
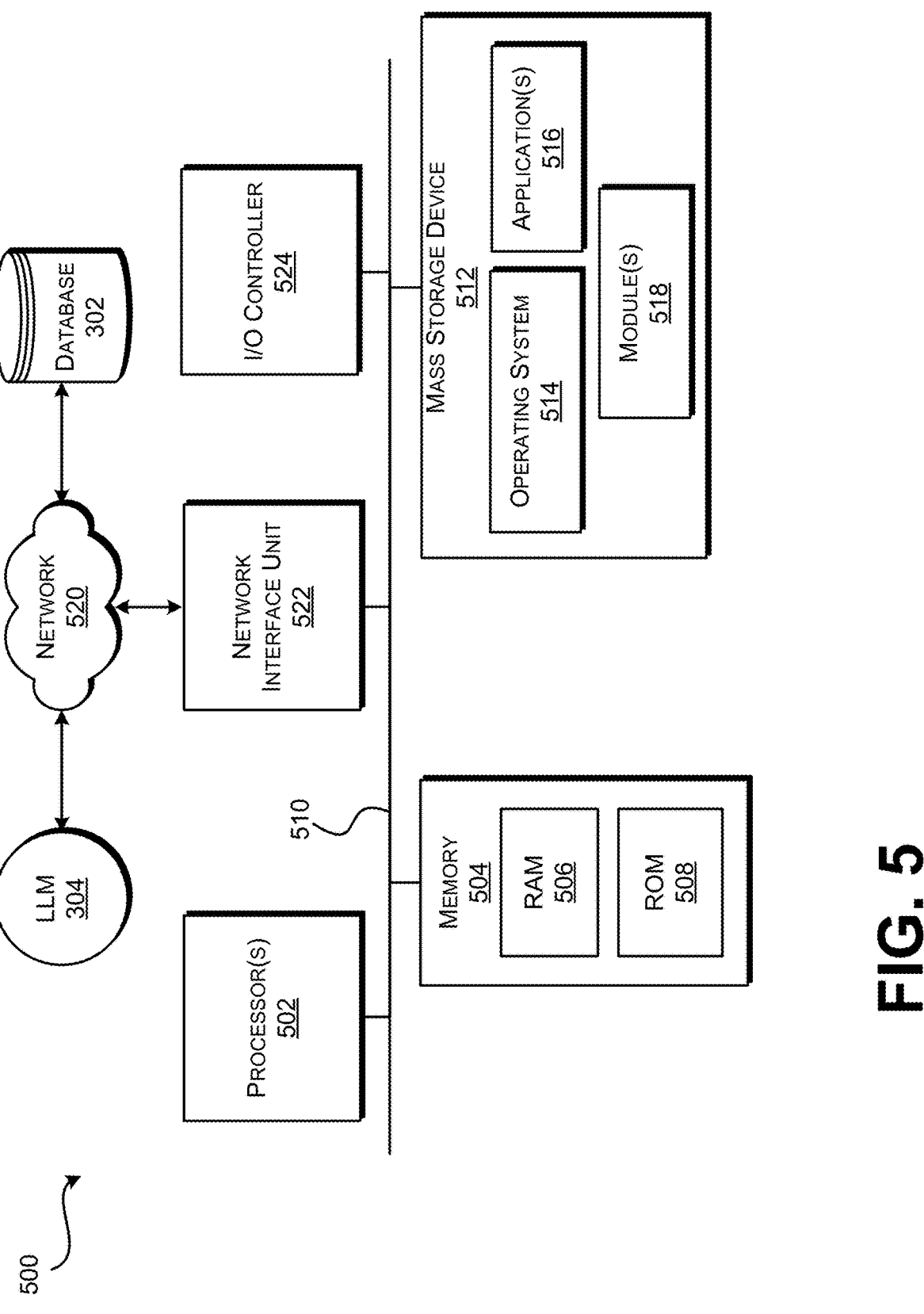
FIG. 5 is a computer architecture diagram illustrating an illustrative computer hardware and software architecture for a computing device capable of implementing aspects of the techniques and technologies presented herein.

FIG. 5 shows details of an example computer architecture 500 for a device, such as a computer or a server configured as part of a cloud-based platform, capable of executing computer instructions (e.g., a module or a component described herein). The computer architecture 500 illustrated in FIG. 5 includes one or more processor(s) 502, a system memory 504, including a random-access memory 506 ("RAM") and a read-only memory ("ROM") 508, and a system bus 510 that couples the memory 504 to the processor(s) 502. The processor(s) 502 may also comprise or be part of a processing system. In various examples, the processor(s) 502 of the processing system are distributed. Stated another way, one processor(s) 502 of the processing system may be located in a first location (e.g., a rack within a datacenter) while another processor(s) 502 of the processing system is located in a second location separate from the first location.

Processing unit(s), such as processor(s) 502, can represent, for example, a CPU-type processing unit, a GPU-type processing unit, a field-programmable gate array (FPGA), another class of digital signal processor (DSP), or other hardware logic components that may, in some instances, be driven by a CPU. For example, illustrative types of hardware logic components that can be used include Application-Specific Integrated Circuits (ASICs), Application-Specific Standard Products (ASSPs), System-on-a-Chip Systems (SOCs), Complex Programmable Logic Devices (CPLDs), and the like.

A basic input/output system containing the basic routines that help to transfer information between elements within the computer architecture 500, such as during startup, is stored in ROM 508. The computer architecture 500 further includes a mass storage device 512 for storing an operating system 514, application(s) 516, modules/components 518, and other data described herein. The operating system 514, application(s) 516, and modules/components 518 may comprise computer-executable instructions implemented by the processor(s) 502.

The mass storage device 512 is communicatively connected to processor(s) 502 through a mass storage controller connected to the bus 510. The mass storage device 512 provides non-volatile storage for the computer architecture 500. It should be appreciated by those skilled in the art that the mass storage device 512 can be any available computer-readable storage medium or communications medium that can be accessed by the computer architecture 500. The mass storage device 512 is a type of memory. Anything shown as stored in the mass storage device 512 may alternatively be stored on another computing device such as one accessible via the network 520.

Computer-readable media can include computer-readable storage media and/or communication media. Computer-readable storage media can include one or more of volatile memory, nonvolatile memory, and/or other persistent and/or auxiliary computer storage media, removable and non-removable computer storage media implemented in any method or technology for storage of information such as computer-readable instructions, data structures, program modules, or other data. Thus, computer storage media includes tangible and/or physical forms of media included in a device and/or hardware component that is part of a device or external to a device, including RAM, static random-access memory (SRAM), dynamic random-access memory (DRAM), phase-change memory (PCM), ROM, erasable programmable read-only memory (EPROM), electrically erasable programmable read-only memory (EEPROM), flash memory, compact disc read-only memory (CD-ROM), digital versatile disks (DVDs), optical cards or other optical storage media, magnetic cassettes, magnetic tape, magnetic disk storage, magnetic cards or other magnetic storage devices or media, solid-state memory devices, storage arrays, network-attached storage, storage area networks, hosted computer storage or any other storage memory, storage device, and/or storage medium that can be used to store and maintain information for access by a computing device.

In contrast to computer-readable storage media, communication media embodies computer-readable instructions, data structures, program modules, or other data in a modulated data signal, such as a carrier wave, or other transmission mechanism. As defined herein, computer-readable storage medium does not include communication medium. That is, computer-readable storage media does not include communications media and thus excludes media consisting solely of a modulated data signal, a carrier wave, or a propagated signal, per se.

According to various configurations, the computer architecture 500 may operate in a networked environment using logical connections to remote computers through a network 520. The network 520 may also provide a connection to the database 302. The LLM 304 may be implemented as a network or "cloud" resource and accessed by the computer architecture 500 via the network 520. The computer architecture 500 may connect to the network 520 through a network interface unit 522 connected to the bus 510. The network interface unit 522 may form the hardware portion of an interface configured to access the database 302 and/or the LLM 304. The respective interfaces may also contain software components on multiple logical levels for constructing interfaces between computer components as is understood by those of ordinary skill in the art. An I/O controller 524 may also be connected to the bus 510 to control communication in input and output devices.

It should be appreciated that the software components described herein may, when loaded into the processor(s) 502 and executed, transform the processor(s) 502 and the overall computer architecture 500 from a general-purpose computing system into a special-purpose computing system customized to facilitate the functionality presented herein. The processor(s) 502 may be constructed from any number of transistors or other discrete circuit elements, which may individually or collectively assume any number of states. More specifically, the processor(s) 502 may operate as a finite-state machine, in response to executable instructions contained within the software modules disclosed herein. These computer-executable instructions may transform the processor(s) 502 by specifying how the processor(s) 502 transitions between states, thereby transforming the transistors or other discrete hardware elements constituting the processor(s) 502.

ILLUSTRATIVE EMBODIMENTS

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method for querying a database (302) comprising: receiving a natural language query (102) containing a reference to a biological sequence (202); generating a custom prompt (200) from the natural language query that includes instructions to access a database look-up tool (310); providing the custom prompt to a large language model (LLM) (304); extracting, by the LLM, the reference to the biological sequence and the instructions to access the database look-up tool; retrieving the biological sequence (306) from the database by the database look-up tool under control of the LLM; and generating an answer (110) containing the biological sequence.

Clause 2. The method of clause 1, wherein the natural language query also contains a modifier and the extracting, by the LLM, further comprises modifying the reference to the biological sequence based on the modifier.

Clause 3. The method of clause 1 or 2, wherein the reference to the biological sequence is a common name of a gene.

Clause 4. The method of any clauses 1 to 3, wherein the custom prompt represents the database look-up tool by a variable.

Clause 5. The method of any of clauses 1 to 4, wherein retrieving the biological sequence further comprises querying the database with the reference to the biological sequence and receiving the biological sequence.

Clause 6. The method of clause 5, wherein the database look-up tool comprises three tools chained together and retrieving the biological sequence further comprises: querying, by a first tool, the database with the reference to the biological sequence and retrieving a database-specific gene identifier; querying, by a second tool, the database with the database-specific gene identifier and retrieving a sequence identifier; and querying, by a third tool, the database with the sequence identifier and retrieving the biological sequence.

Clause 7. The method of any of clauses 1 to 6, further comprising: determining that the reference to the biological sequence resolves to more than one biological sequence in the database, and generating a response that requests additional description of the biological sequence.

Clause 8. Computer-readable storage media comprising instructions that, when executed by a computing device, cause the computing device to perform the method of any of clauses 1 to 7.

Clause 9. A system comprising a processor and a memory storing instructions that cause the system to perform the method of any of clauses 1 to 7.

Clause 10. A system for querying a database (302) comprising: a processor (502); a memory (504); an interface (522) configured to access a large language model (LLM) (304); a custom prompt generator (308) configured to generate a custom prompt (200) from a natural language query (102) containing a reference to a biological sequence (202) and provide the custom prompt to the LLM, wherein the custom prompt includes instructions to access a database look-up tool (310); and the database look-up tool configured to submit queries and obtain data from the database.

Clause 11. The system of clause 10, wherein the interface also comprises an orchestration framework configured to connect the LLM to the custom prompt generator and to the database look-up tool.

Clause 12. The system of clause 10 or 11, wherein the custom prompt generator is further configured to generate the custom prompt based on a modifier contained in the natural language query such the reference to the biological sequence is modified based on the modifier.

Clause 13. The system of any of clauses 10 to 12, wherein the custom prompt generator is further configured to generate the custom prompt with a variable that represents the database look-up tool.

Clause 14. The system of any of clauses 10 to 13, wherein the database look-up tool comprises a first tool that is configured to query the database with the reference to the biological sequence and receive a database-specific gene identifier.

Clause 15. The system of clause 14, wherein the database look-up tool comprises a second tool that is configured to query the database with the database-specific gene identifier and retrieve a sequence identifier.

Clause 16. The system of clause 15, wherein the database look-up tool comprises a third tool that is configured to query the database with the sequence identifier and retrieve the biological sequence.

Clause 17. Computer-readable storage media comprising instructions that, when executed by a computing device (500), cause the computing device to perform actions comprising: receiving a natural language query (102) containing a reference to a biological sequence (202); generating a custom prompt (200) from the natural language query that includes instructions to access a database look-up tool (310); providing the custom prompt to a large language model (LLM) (304); extracting, by the LLM, the reference to the biological sequence and the instructions to access the database look-up tool; retrieving the biological sequence (306) from a database (302) by the database look-up tool under control of the LLM; and generating an answer (110) containing the biological sequence.

Clause 18. The computer-readable storage media of clause 17, wherein the natural language query also contains a modifier and the extracting, by the LLM, further comprises modifying the reference to the biological sequence based on the modifier.

Clause 19. The computer-readable storage media of clause 17 or 18, wherein the custom prompt represents the database look-up tool by a variable.

Clause 20. The computer-readable storage media of any of clauses 17 to 19, wherein retrieving the biological sequence further comprises querying the database with the reference to the biological sequence and receiving the biological sequence.

Clause 21. The computer-readable storage media of any of clauses 17 to 20, wherein the database look-up tool comprises three tools chained together and retrieving the biological sequence further comprises: querying, by a first tool, the database with the reference to the biological sequence and retrieving a database-specific gene identifier; querying, by a second tool, the database with the database-specific gene identifier and retrieving a sequence identifier; and querying, by a third tool, the database with the sequence identifier and retrieving the biological sequence.

Clause 22. The computer-readable storage media of any of clauses 17 to 21, wherein the actions further comprise: determining that the reference to the biological sequence resolves to more than one biological sequence in the database, and generating a response that requests additional description of the biological sequence.

CONCLUSION

While certain example embodiments have been described, including the best mode known to the inventors for carrying out the invention, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. Skilled artisans will know how to employ such variations as appropriate, and the embodiments disclosed herein may be practiced otherwise than specifically described. The accompanying claims and their equivalents are intended to cover such forms or modifications as would fall within the scope and spirit of certain of the inventions disclosed herein.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced.

It should be appreciated that any reference to "first," "second," etc. elements within the Summary and/or Detailed Description is not intended to and should not be construed to necessarily correspond to any reference of "first," "second," etc. elements of the claims. Rather, any use of "first" and "second" within the Summary, Detailed Description, and/or claims may be used to distinguish between two different instances of the same element (e.g., two different tools).

In closing, although the various configurations have been described in language specific to structural features and/or methodological acts, it is to be understood that the subject matter defined in the appended representations is not necessarily limited to the specific features or acts described. Rather, the specific features and acts are disclosed as example forms of implementing the claimed subject matter.

The invention claimed is:

1. A method for querying a database comprising:
   receiving a natural language query containing a reference to a biological sequence;
   generating a custom prompt from the natural language query that includes instructions to access a database look-up tool;
   providing the custom prompt to a large language model (LLM);
   extracting, by the LLM, the reference to the biological sequence and the instructions to access the database look-up tool;
   retrieving the biological sequence from the database by the database look-up tool under control of the LLM, wherein the database look-up tool comprises three tools chained together and retrieving the biological sequence further comprises:
   querying, by a first tool, the database with the reference to the biological sequence and retrieving a database-specific gene identifier;
   querying, by a second tool, the database with the database-specific gene identifier and retrieving a sequence identifier; and
   querying, by a third tool, the database with the sequence identifier and retrieving the biological sequence; and
   generating an answer containing the biological sequence.

2. The method of claim 1, wherein the natural language query also contains a modifier and the extracting, by the LLM, further comprises modifying the reference to the biological sequence based on the modifier.

3. The method of claim 1, wherein the reference to the biological sequence is a common name of a gene.

4. The method of claim 3, wherein the first tool generates synonyms to the common name of the gene and submits one query for each synonym to the database.

5. The method of claim 1, wherein the custom prompt represents the database look-up tool by a variable.

6. The method of claim 1, further comprising:
   determining that the reference to the biological sequence resolves to more than one biological sequence in the database, and
   generating a response that requests additional description of the biological sequence.

7. The method of claim 1, wherein the sequence identifier is a transcript ID, a protein ID, or a GenInfo Identifier (GI) number.

8. A system for querying a database comprising:
   a processor;
   a memory;
   an interface configured to receive a natural language query containing a reference to a biological sequence and display an answer received from a large language model (LLM), the answer containing the biological sequence;
   a custom prompt generator configured to generate a custom prompt from the natural language query containing the reference to the biological sequence and provide the custom prompt to the LLM, wherein the custom prompt includes instructions to access a database look-up tool; and
   the database look-up tool configured to submit queries and obtain data from the database, the database look-up tool comprising:
      a first tool that is configured to query the database with the reference to the biological sequence and receive a database-specific gene identifier; and
      a second tool that is configured to query the database with the database-specific gene identifier and retrieve a sequence identifier.

9. The system of claim 8, wherein the interface also comprises an orchestration framework configured to connect the LLM to the custom prompt generator and to the database look-up tool.

10. The system of claim 8, wherein the custom prompt generator is further configured to generate the custom prompt based on a modifier contained in the natural language query such that the reference to the biological sequence is modified based on the modifier.

11. The system of claim 8, wherein the custom prompt generator is further configured to generate the custom prompt with a variable that represents the database look-up tool.

12. The system of claim 8, wherein the database look-up tool comprises a third tool that is configured to query the database with the sequence identifier and retrieve the biological sequence.

13. The system of claim 8, wherein the reference to the biological sequence is a common name of a gene.

14. The system of claim 13, wherein the first tool generates synonyms to the common name of the gene and submits one query for each synonym to the database.

15. Computer-readable storage media comprising instructions that, when executed by a computing device, cause the computing device to perform actions comprising:

receiving a natural language query containing a reference to a biological sequence;

generating a custom prompt from the natural language query that includes instructions to access a database look-up tool;

providing the custom prompt to a large language model (LLM);

extracting, by the LLM, the reference to the biological sequence and the instructions to access the database look-up tool;

retrieving the biological sequence from a database by the database look-up tool under control of the LLM, wherein the database look-up tool comprises three tools chained together and retrieving the biological sequence further comprises:

querying, by a first tool, the database with the reference to the biological sequence and retrieving a database-specific gene identifier;

querying, by a second tool, the database with the database-specific gene identifier and retrieving a sequence identifier; and querying, by a third tool, the database with the sequence identifier and retrieving the biological sequence; and generating an answer containing the biological sequence.

16. The computer-readable storage media of claim 15, wherein the natural language query also contains a modifier and the extracting, by the LLM, further comprises modifying the reference to the biological sequence based on the modifier.

17. The computer-readable storage media of claim 15, wherein the custom prompt represents the database look-up tool by a variable.

18. The computer-readable storage media of claim 15, wherein the actions further comprise:

determining that the reference to the biological sequence resolves to more than one biological sequence in the database, and generating a response that requests additional description of the biological sequence.

19. The computer-readable storage media of claim 15, wherein the reference to the biological sequence is a common name of a gene.

20. The computer-readable storage media of claim 19, wherein the first tool generates synonyms to the common name of the gene and submits one query for each synonym to the database.

\* \* \* \* \*